United States Patent [19]

Wood et al.

[11] 3,976,064

[45] Aug. 24, 1976

[54] INTERMITTENT MANDATORY ASSISTED VENTILATION SYSTEM FOR POSITIVE PRESSURE BREATHING APPARATUS

[76] Inventors: William W. Wood, 478 Shadowood, NW., Comstock Park, Mich. 49321; James E. Greenwood, 675 Nordberg, NW., Grand Rapids, Mich. 49503; Walter M. Clements, 8984 Thirteen Mile Road, Rockford, Mich. 49341

[22] Filed: Mar. 11, 1975

[21] Appl. No.: 557,254

[52] U.S. Cl. .................................. 128/145.8
[51] Int. Cl.² ................................ A61M 16/00
[58] Field of Search........... 128/145.5, 145.6, 145.8, 128/146.5, 2.08, 188, 142, 142.2, 195, 208–210

[56] References Cited
UNITED STATES PATENTS

| | | |
|---|---|---|
| 3,659,598 | 5/1972 | Peters et al. ..................... 128/145.8 |
| 3,730,180 | 5/1973 | Davison ........................... 128/145.6 |
| 3,834,382 | 9/1974 | Lederman et al. ................ 128/145.8 |

*Primary Examiner*—Robert W. Michell
*Assistant Examiner*—Henry J. Recla
*Attorney, Agent, or Firm*—McGarry & Waters

[57] ABSTRACT

A respiration system for weaning patients from a respirator wherein a mandatory ventilation assist is provided to the patient upon inspiration after predetermined time intervals. A sensitivity mechanism for sensing inspiration by the patient and for actuating the mandatory ventilation assist is desensitized or rendered inoperative during a predetermined time interval in which the patient will be required to breathe normally without assist. At the end of the time interval, the sensitivity mechanism is again rendered operative for the mandatory ventilation assist. In the event that the patient does not trigger the sensitivity mechanism within a second given period of time following the end of the time interval, a mandatory ventilation assist is provided.

16 Claims, 1 Drawing Figure

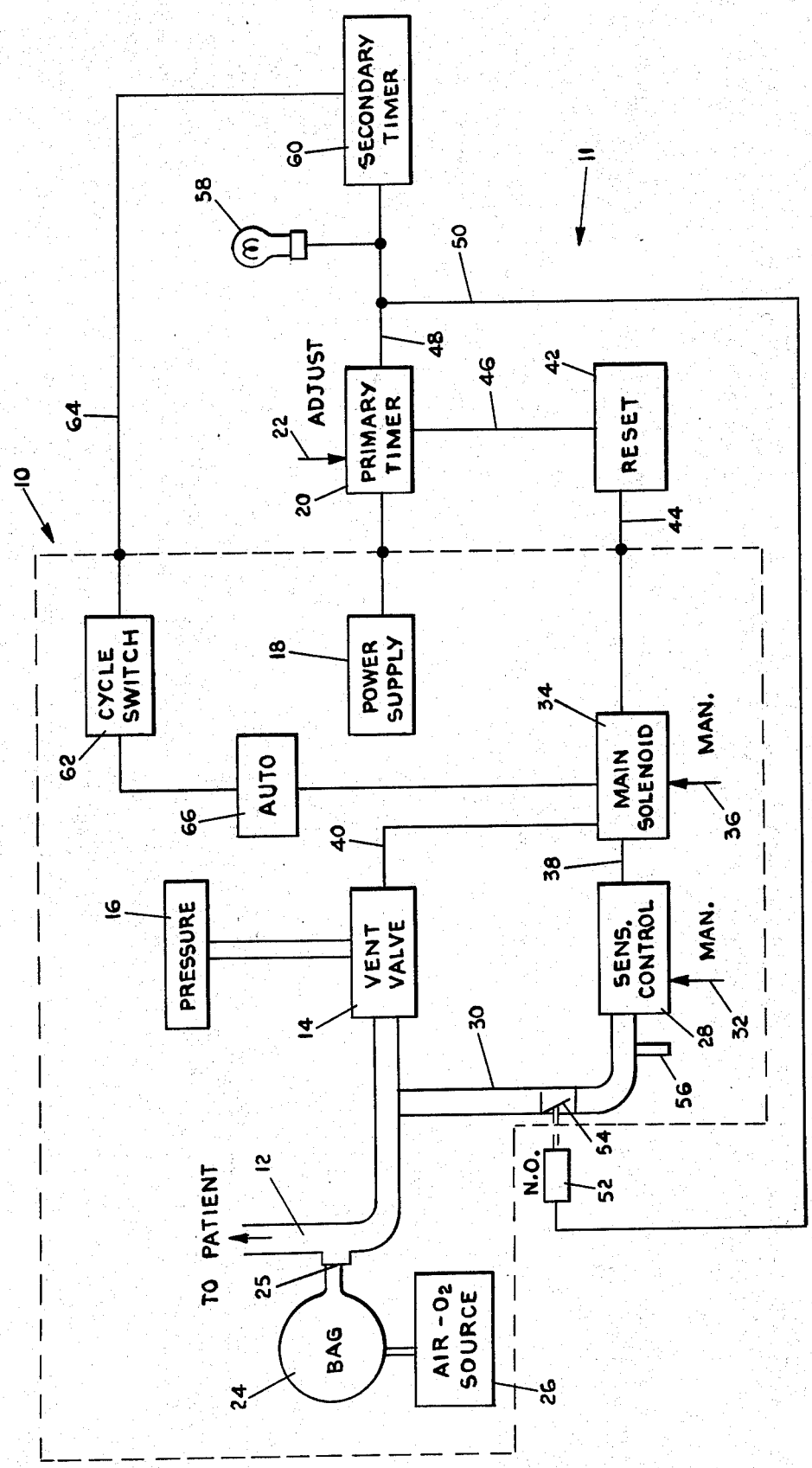

INTERMITTENT MANDATORY ASSISTED VENTILATION SYSTEM FOR POSITIVE PRESSURE BREATHING APPARATUS

BACKGROUND OF INVENTION

1. Field of Invention

This invention relates to a respiration system. In one of its aspects, the invention relates to a respiration system in which an inspiration sensitive ventilation system is rendered inoperative during a given time interval and operative thereafter for a single ventilation assist before weaning a patient from a respiration system.

2. State of the Prior Art

Respiration systems are well known and are in common use. An example of a respirator system is the MA-1 ventilator sold by Puritan-Bennett Corporation of Kansas City, Missouri. Respirator systems are also disclosed in many U.S. patents, including the U.S. patents to Bartels U.S. Pat. No. 3,664,361, Beasley U.S. Pat. No. 3,368,555, Beasley U.S. Pat. No. 3,395,669, and Weigl U.S. Pat. No. 3,817,246.

Respirators operate in basically two modes. In one mode, a ventilation assist is provided to a patient upon inhalation at every breath. In another mode, a ventilation assist is provided at timed intervals for the patient regardless of the point in the respiration cycle.

It has been found that patients become dependent on ventilation assist from a respiration system and prefer to rely on the respirator rather than the patients' own respiratory system. Recently, the timed interval mode of the respiration system has been used in an attempt to wean the patients from the respirator system. In this mode, a ventilation assist is provided to the patient after predetermined periods of time between which the patient must breathe on his own. Presently, the times provided in the machines do not have a long enough cycle times to permit complete weaning of the patients from the machine. Further, and perhaps more important, the use of a mandatory assist after a predetermined time is psychologically undesirable for the patient because the patient tends to be apprehensive as to when the mandatory assist will be supplied. Possibly, the mandatory assist would be provided at the exhilation stage of the patient's breathing cycle. Fortuitously, it may be applied during the inhalation stage. Even if applied during the inhalation stage, it may be at an inappropriate period in the patient's respiratory cycle.

SUMMARY OF THE INVENTION

According to the invention, a respiration system has been provided for weaning patients from the respirator. The respiration system has a breathing tube having an open outlet end for delivering oxygen-containing gas to a patient and an input end. Means are connected to the input end of the breathing tube for supplying oxygen-containing gas to the breathing tube at a first pressure near or at atmospheric pressure. Means are provided for supplying oxygen-containing gas at a second pressure higher than the first pressure for the ventilation assist, the second gas supply means including a ventilation valve coupled to the input end of the breathing tube. A sensitivity control means is coupled to the breathing tube for determining the pressure therein with the sensitivity control means including means for actuating the ventilation valve responsive to the presence of a third pressure in the breathing tube. The third pressure is less than the first pressure. The third pressure, which is normally adjustable, corresponds to the inspiration pressure provided by the patient.

According to the invention, a timer control means is coupled to the sensitivity control means and includes a timer for measuring a given time interval, means for desensitizing the sensitivity control means so as to render the same inoperative, and means coupling the timer to the desensitizing means for desensitizing the sensitivity control means during each cycle of the time. The desensitizing means is released upon expiration of the time interval so that the sensitivity control means again becomes operative to provide a mandatory ventilation assist to the patient at the next inspiration portion of the respiratory cycle thereof. Upon inspiration and upon the operation of the ventilation valve, the timer is reset and the sensitivity control means is again desensitized so that the patient breathes normally without a ventilation assist. The desensitizing means desirably is a valve which blocks communication between the sensitivity control means and the breathing tube. The desensitizing means is positioned in a conduit which couples the sensitivity control means to the breathing tube. Means are provided in the conduit for equalizing the pressure between the sensitivity control means and the blocking valve.

Desirably, means are provided for actuating the ventilation valve to supply a mandatory assist to the breathing tube in the event that the ventilation valve has not operated within a predetermined time after the expiration of the time interval determined by the timer. Desirably, means are provided for adjusting the time interval of the timer control means.

The desensitizing means is desirably biased into an inoperative condition with respect to the sensitivity control means and desensitizes said sensitivity control means when signal is applied thereto from the timer.

BRIEF DESCRIPTION OF THE DRAWINGS

The invention will now be described with reference to the accompanying drawing which schmatically shows an embodiment of the invention.

DESCRIPTION OF THE PREFERRED EMBODIMENT

Referring now to the drawing, there is shown in schematic form a respirator or positive pressure breathing apparatus having an intermittent mandatory assisted ventilation system. Positive pressure breathing apparatus per se are well known and are described in part in the United States patent to Bartels U.S. Pat. No. 3,664,361, for example. A known positive pressure breathing apparatus is indicated generally by the numeral 10 and is enclosed within the phantom lines in the drawing.

Generally, the positive pressure breathing apparatus has a patient supply duct 12 which is connected to the patient at an output end through either a breathing mask or the mouthpiece (not shown) through which the patient breathes. Means are provided (not shown) to exhaust exhalations from the tube 12. The patient supply duct 12 is connected at an input end to a ventilation valve 14 which in turn is connected to a source 16 of oxygen-containing gas under pressure. An air bag 24 is connected to the patient supply duct 12 through a flapper check valve 25. Air or oxygen enriched air is supplied to the bag 24 from an air and oxygen source 26 such as cylinders of air and oxygen under pressure or such as an air supply pipe. The air and oxygen source 26 maintains a predetermined low pressure of air or oxygen enriched air within the bag 24 so that the patient can breathe easily from the bag 24. The valve 25 thus opens upon inhalation and closes when the pressure in the tube 12 exceeds the pressure in the bag 24. Such condition occurs during exhalations and during ventilated assists from the pressure source 16.

The ventilation valve 14 is controlled by a main solenoid 34 having a manual adjustment 36. The main solenoid 34 is connected to the ventilator valve through a lead line 40. The main solenoid 34 is controlled either by a sensitivity control 32 or by an automatic cycling mechanism 66. A cycle switch 62 controls the automatic cycling mechanism 66 so that the main solenoid 34 is operated at regular intervals to open the ventilation valve 14 and supply a pulse of air, or air mixed with oxygen, under pressure to the patient through the patient supply duct 12.

A sensitivity control mechanism 28 is connected through a small sensing tube 30 to the patient supply duct 12 and operates the main solenoid 34 in the alternate mode of sensitivity control. A manual adjustment 32 is provided on the sensitivity control 28 to adjust the pressure at which the sensitivity control is operable to actuate the main solenoid 34.

The foregoing has been a description of an intermittent positive pressure breathing apparatus, such as the MA-1 ventilation currently marketed by Puritan-Bennett Corporation of Kansas City, Missouri. In normal operation of the sensitivity control, upon inspirations by a patient at a predetermined negative pressure (below atmospheric pressure), the sensitivity control 28 will operate the main solenoid 34 to open the ventilation valve 14 to provide a pulse of air under pressure from the source 16. Upon exhalation, the sensitivity control closes. The cycle begins again upon inhalation.

In the automatic cycle control mode, the cycle switch 62 is operated to commence operation of the automatic cycle control 66. In this mode, the sensitivity control 28 is desensitized and not operable. The automatic cycling control has a timer which operates the main solenoid 34 (through conventional relays) to operate the ventilation valve 14 after predetermined time intervals. The automatic cycle control mode thus provides a ventilation assist at a given time instant regardless of the particular point in the patient's respiration cycle.

The intermittent mandatory assist ventilation system of the invention is generally designated by the numeral 11. In this system, a primary timer 20 is connected to a power supply 18 of the breathing apparatus 10 (or can be connected to a separate power supply. An input for the timer 20 is connected to a reset relay 42 through lead 46. The reset relay 42 is in turn connected to the main solenoid 34 through lead 44. A manual adjustment 22 is provided on the primary timer 20 to adjust the timing cycle. The function of the primary timer 20 is to time out a cycle of, for example, one to six minutes, or even longer, and upon expiration of the timer to deliver an output signal to open a circuit. This time interval allows the patient to draw one or more unassisted breaths. The timer 20 is reset to zero by an input signal from the reset relay 42. Timing circuits which perform this function are well known.

Conventionally, relays are provided in the timing circuit. The relays are operated upon the expiration of the timer cycle so that a circuit will be opened or closed. In the case of the system illustrated in the drawing, the timer circuit includes a timer output lead 50 and a solenoid 52. A valve 54 in sensing tube 30 is controlled by the solenoid 52 which is biased so that the valve is normally open. Thus, when current is flowing through the circuit, including the solenoid 52, the valve 54 is closed. At the end of the timer cycle for the timer 20, the circuit is opened and the solenoid 52 opens the valve 54.

A timer output lead 48 is also connected to a secondary timer 60. The expiration of the primary timer commences operation of the secondary timer 60 and illuminates the lamp 58 in addition to opening the valve 54. The secondary timer 60 is connected to the cycle switch 62 through lead 64. The secondary timer is of a construction and function similar to the primary timer 20. The secondary timer 60 begins to time upon a signal from the primary timer at the end of the primary timer cycle. In actual practice the primary timer at the end of the time cycle activates a relay which commences timing in the timer 60. At the end of the time cycle for the timer 60, a relay is activated to throw the cycle switch 62. The secondary timer is reset to zero by the primary timer 20 when the primary timer 20 is reset to zero.

A small bleed tube 56 is provided in the small tube 30 between the valve 54 and the sensitivity control 58 to equalize the pressure therein upon closing the valve 54.

The operation of the IMAV system will now be described. At the start of the cycle, the valve 54 is open and the ventilation valve 14 is closed. Inhalation by the patient operates the sensitivity control 28 to activate the solenoid to open the ventilation valve 14. Thus a pressurized pulse of air or ventilation assist is supplied to the patient through line 12. At the end of the inhalation cycle, the main solenoid valve 34 resets the primary timer 20 and the secondary timer 60 to zero through the reset relay 42. As the timer begins its timing cycle, the solenoid 52 is energized by the primary timer 20 so that valve 54 closes. At the end of the primary timer cycle, the solenoid 52 will be de-energized to open the valve 54 and permit another ventilation assist upon inhalation from the patient. The completion of the time cycle for the primary timer 20 commences the operation of the secondary timer 60. If the patient has not drawn a breath and activated the sensitivity control during the cycle of the secondary timer, the secondary timer 60 will operate the cycle switch 62 as, for example, through a relay (not shown) to commence operation of the automatic cycle control 66 for a single ventilation assist. Upon opening and closing of the main solenoid 34, the primary timer and secondary timer will be reset for another cycle. The secondary timer will have a relatively short time period of, for example, ten seconds so that the patient obtains the assist if he does not activate the sensitivity control 28 within a short period of time.

The invention thus provides a mechanism for weaning a patient from a respirator system by providing relatively long periods when the patient must breath normally without assistance from the machine. However, at regular intervals an assist is provided upon inhalation by the patient. The assist thus comes responsive to the need of the patient and occurs during the inhalation phase of the patient's respiration cycle.

Reasonable variation and modifications are possible within the scope of the foregoing disclosure without departing from the spirit of the invention which is embodied in the accompanying claims.

The embodiments of the invention in which an exclusive property or privilege is claimed are defined as follows:

1. In a respiration system having a breathing tube with an open output end for delivering oxygen-containing gas to a patient and an input end;
    means connected to the input end of the breathing tube for supplying oxygen-containing gas to the breathing tube at a first pressure near or at atmospheric pressure for unassisted breathing by the patient;
    means for providing oxygen-containing gas to the breathing tube at a second pressure higher than the first pressure for providing a ventilation assist to the patient, said second higher pressure gas providing means including a ventilation valve coupled to said input end of said breathing tube for controlling the flow of oxygen-containing gas at said second pressure to said breathing tube;
    sensitivity control means coupled to said breathing tube for determining the pressure therein, said sensitivity control means including means for actuating said ventilation valve responsive to the presence of a third pressure in said breathing tube, said third pressure being below said first pressure, said sensitivity control means providing a ventilation assist to the patient responsive to an inspiration by the patient;
    the improvement which comprises:
    timing means for measuring a given time interval sufficient to allow the patient to inhale and exhale at least one unassisted breath, means for desensitizing said sensitivity control means so as to render the same inoperative; and means coupling said timing means to said desensitizing means for desensitizing said sensitivity control means during each given time interval of said timer such that the ventilation valve is inoperative during the time interval to allow the patient to inhale and exhale at least one unassisted breath from said oxygen-containing gas at said first pressure, and for releasing said desensitizing means upon expiration of said time interval such that said sensitivity control means is rendered operative subsequent to each of said time intervals, thereby providing subsequent assisted ventilation for the patient from said oxygen-containing gas at said second pressure;
    said breathing tube being open to said first pressure oxygen-containing gas during said time interval;
    whereby said respirator system provides a single intermittent mandatory assisted ventilation upon inspiration by the patient after expiration of the time interval during which the patient breaths unassisted from the first pressure oxygen-containing gas.

2. A respiration system according to claim 1 wherein said desensitizing means comprises means for blocking communication between said sensitivity control means and said breathing tube.

3. A respiration system according to claim 2 and further comprising a sensing conduit coupling said sensitivity control means to said breathing tube and means for equalizing the pressure in said sensing conduit between said sensitivity control means and said blocking means.

4. A respiration system according to claim 3 and further comprising means for actuating said ventilation valve to supply a mandatory breath to said breathing tube in the event that said ventilation valve has not operated within a predetermined time after expiration of said time interval; means for resetting said timing means upon operation of said ventilation valve; and means for adjusting the time of said interval timing means.

5. A respiration system according to claim 2 wherein said desensitizing means is biased in an inoperative condition with respect to said sensitivity control means to desensitize said sensitivity control means when a signal is applied thereto from said timer means.

6. A respiration system according to claim 1 and further comprising means for actuating said ventilation valve to supply a mandatory breath to said breathing tube in the event that said ventilation valve has not operated within a predetermined time after expiration of said given time interval.

7. A respiration system according to claim 1 and further comprising means for resetting said timing means upon operation of said ventilation valve.

8. A respiration system according to claim 1 and further comprising means for adjusting the time interval of said timing means.

9. A respiration system according to claim 1 and further comprising visible signal means coupled to said timing means for indicating a visible signal at the expiration of the time interval of said timing means.

10. A respiration system according to claim 1 wherein the time interval is one to six minutes.

11. An intermittent mandatory assisted ventilation system for a respiration system having a source of oxygen-containing gas at a first pressure, a patient breathing tube, and a ventilation valve connecting said oxygen-containing gas under a first pressure to said patient breathing tube, a sensitivity control means coupled to the breathing tube for detecting the pressure therein, the sensitivity control means including means for actuating the ventilation valve to open responsive to the presence of an inspiration pressure in the breathing tube; and a source of an oxygen-containing gas at a pressure lower than said first pressure and at or near atmospheric pressure for unassisted breathing connected to said patient breathing tube;
    said intermittent mandatory assisted ventilation system comprising:
    timing means for measuring a given time interval sufficient to allow at least one unassisted inhalation and exhalation cycle by the patient; means for desensitizing said sensitivity control means so as to render the same inoperative, and means coupling the timing means to the desensitizing means for desensitizing the sensitivity control means during each given time interval and for releasing the desensitizing means upon expiration of the time interval to allow the patient to draw at least one breath from the lower pressure oxygen source and thereafter to provide ventilation assistance to the patient;
        said breathing tube being open to said lower pressure oxygen-containing gas for unassisted breathing during the time interval of the timing means
        whereby said respiration system provides a single intermittent mandatory assisted ventilation upon inspiration by the patient after expiration of the time interval.

12. An intermittent mandatory assisted ventilation system according to claim 11 and further comprising means adapted to be coupled to said ventilation valve for resetting said timing means upon operation of said ventilation valve.

13. An intermittent mandatory assisted ventilation system according to claim 11 wherein said timing means includes a first timer for measuring said first mentioned time interval and a second timer coupled to said first timer for measuring a second predetermined time interval, said second timer being actuated by said first timer after the expiration of said first time interval, and means associated with said second timer for delivering a control signal to the ventilation valve after the expiration of said second predetermined time subsequent to the expiration of the first time interval in the event the ventilation valve has not been operated after expiration of the predetermined time of the second mentioned timer.

14. An intermittent mandatory assisted ventilation system according to claim 13 and further comprising means for resetting the timing means to reset said first timer to zero and to reset said second timer to zero upon operation of said ventilation valve.

15. An intermittent mandatory assisted ventilation system according to claim 11 and further comprising means for resetting said timing means to zero upon operation of said ventilation valve.

16. An intermittent mandatory assisted ventilation system according to claim 11 wherein said given time interval is in the range of 1 to 6 minutes.

* * * * *